United States Patent [19]

Carson et al.

[11] Patent Number: 4,927,812

[45] Date of Patent: May 22, 1990

[54] MORPHOLINYL SILANES AND USE FOR CONTROL OF PLANT DISEASES CAUSED BY FUNGI

[75] Inventors: Chrislyn M. Carson, Midland, Mich.; Leonard G. Copping, Saffron Walden, England; Robert J. Ehr, Vallejo, Calif.; Melvin H. Gitlitz, Edison; Maynard W. McNeil, Washington, both of N.J.; Peter F. S. Street, Marlborough; John W. Liebeschuetz, Wantage, both of England

[73] Assignees: Atochem North America, Inc., Somerville, N.J.; The Dow Chemical Company, Midland, Mich.

[21] Appl. No.: 322,140

[22] Filed: Mar. 13, 1989

Related U.S. Application Data

[63] Continuation-in-part of Ser. No. 111,374, Oct. 21, 1987, abandoned.

[51] Int. Cl.$^5$ .......................... A01N 55/00; C07F 7/10
[52] U.S. Cl. .......................................... 514/63; 544/69
[58] Field of Search ............................. 544/69; 514/63

[56] References Cited

U.S. PATENT DOCUMENTS 4,762,826  8/1988  Eckhardt .......................... 544/69 X

FOREIGN PATENT DOCUMENTS 148026   7/1985  European Pat. Off. .
241429  10/1987  European Pat. Off. .

OTHER PUBLICATIONS

Lukevics et al., Latv. PSR Zinat. Akad Vestis, No. 3, (1978), pp. 83–86 (abstract).

Primary Examiner—Richard L. Raymond
Attorney, Agent, or Firm—S. Preston Jones; Ronald G. Brookens

[57] ABSTRACT

Aryl substituted morpholinyl silanes, their preparation, compositions containing said compounds and their use as agricultural fungicides are disclosed.

57 Claims, No Drawings

MORPHOLINYL SILANES AND USE FOR CONTROL OF PLANT DISEASES CAUSED BY FUNGI

CROSS REFERENCE TO RELATED APPLICATION

This application is a continuation-in-part of co-pending U.S. application Ser. No. 111,374, filed October 21, 1987, now abandoned.

BACKGROUND OF THE INVENTION

1. Field of the Invention

This invention relates to certain novel aryl substituted morpholinyl silanes, compositions containing said compounds and to their use as agricultural fungicides.

2. Description of the Prior Art

Various aminosilanes are disclosed in the chemical literature. The in vivo fungicidal activity of several aminosilanes containing a substituted phenyl group or an N-morpholinopropyl group bonded to silicon is discussed in an article by E. Lukevics et al. (Latv. PSR Zinat. Akad. Vestis, Kim. Serv. 1978, (3) 343-349)). These compounds exhibit at most only moderate activity against wheat rust, tomato late blight and cucumber powdery mildew. None of the compounds disclosed in this reference contain both a substituted aryl group and an aminoalkyl group wherein the nitrogen atom is part of a morpholine ring.

Additionally, U.S. Pat. No. 4,762,826 discloses the fungicidal activity of several silanes containing an N-morpholinomethyl or substituted N-morpholinomethyl group bonded to silicon against fungi which attack plants.

DESCRIPTION OF THE INVENTION

This invention relates to certain novel aryl substituted morpholinyl silanes and their salts; to fungicidal compositions containing said silanes and to methods for controlling phytopathogenic fungi employing compositions containing said silanes as the active material or component therein. In another aspect, the invention relates to fungicidal compositions containing these compounds and their salts, either alone or in admixture, with other active components.

The aryl substituted morpholinyl silanes of the present invention correspond to the formula

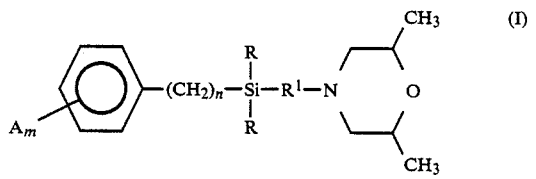

wherein
each A independently represents halogen, $C_1$-$C_4$ alkyl, $C_1$-$C_4$ alkoxy, phenyl, phenoxy or halomethyl;
each R independently represents $C_1$-$C_4$ alkyl;
n represents the integer 0, 1 or 2;
m represents an integer of from 0 to 5; and
$R^1$ represents an alkylene group of the formula

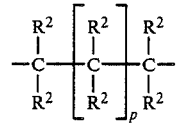

where each $R^2$ independently represents hydrogen or $C_1$-$C_3$ straight chain alkyl and p represents an integer of from 1 to 4, with the proviso that the total number of carbon atoms in $R^1$ is from 3-6.

In the present specification and claims, the terms "$C_1$-$C_4$ alkyl" and "$C_1$-$C_4$ alkoxy" are employed to designate straight or branched chain alkyl or alkoxy groups of 1 to 4 carbon atoms.

The term "halomethyl" as used in the present specification and claims designates a methyl radical containing from 1 to 3 halogen atoms, which may be the same or different.

The term "halogen" represents Br, Cl or F.

Preferred compounds of the invention are those on which A is trifluoromethyl, $C_1$-$C_4$ alkyl, Cl or F. More preferred compounds are those where $R^1$ is $-(CH_2)_3-$, $-(CH_2)_4-$ or

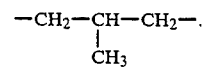

All the organic and inorganic acids which form stable physiologically acceptable salts are suitable for salt formation with compounds of the Formula I. Examples of salts are chlorides, bromides, iodides, sulphates, phosphates, acetates, oxalates, fumarates, malonates, alkylsulphonates, arylsulphonates, alkylarylsulphonates, octanoates and oleates.

The salts are obtained by mixing the corresponding acid with the free amine of Formula I, if necessary in an inert solvent, distilling off the solvent and recrystallizing the residue as necessary. Alternately, water soluble salts such as phosphates and acetates may be prepared as aqueous solutions, for ease of formulation, by neutralization of the free amine in an equimolar amount of the acid. Oil soluble acid derivatives such as the oleate may also be prepared by a similar means in an organic solvent such as xylene.

The compounds of the present invention effectively control a variety of undesirable fungi which infest useful plant crops. Many of the compounds are particularly effective against organisms such as *Erysiphe graminis* which cause powdery mildew of grains, particularly barley and wheat. Compositions containing the present compounds can be applied to the roots, seeds or foliage of the barley or other plants, and will kill or control the growth of various fungi without damaging the commercial value of said plants. Many of these compositions are unique because of their systemic action and because of the very low levels of chemical required to control powdery mildew.

These chemicals may be prepared as dusts, wettable powders, flowable concentrates, or emulsifiable concentrates.

The invention includes within its scope a method for the control of fungus diseases attacking plants or plant parts which method comprises applying to their plants, the plant parts or to the organisms or to their habitats one or more of the compositions in accordance with the invention.

Another advantage of the present invention is that a single application of the compositions can provide a residual control of powdery mildew diseases over an extended period. Also, the compounds can be effective in eliminating established barley powdery mildew infestation. Furthermore, many compounds have been found to be translocated in plants and, thus, can provide a systemic protection against powdery mildew.

The method of the present invention comprises contacting plants, especially cereal grain plants, with a fungicidal amount of one or more of the compounds. The present invention also embraces the employment of a liquid, powder, dust or granular composition containing one or more of the active compounds in intimate admixture with inert, non-phytotoxic materials, known in the art as agricultural adjuvants and/or carriers, in solid or liquid form. Thus, for example, the active compound(s) can be admixed with one or more additives including organic solvents, petroleum distillates, water or other liquid carriers, surface active dispersing agents, and finely divided inert solids. In such compositions, the active ingredients are present in a concentration from about 2 percent to about 95 percent by weight, preferably 10 percent to about 95 percent by weight and most advantageously 10 percent to about 75 percent by weight. The compound can be employed in the form of diluted flowable compositions or a wettable powder composition containing 2 to 10,000 ppm of morpholinyl silane compound, preferably 10 to 600 ppm are employed. When the carrier contains a surface active agent, from about 0.1 to about 20 percent by weight of the active ingredient is advantageously employed. Depending upon the concentration in the composition, such augmented compositions are adapted to be employed for the control of the undesirable fungi or employed as concentrates and subsequently diluted with additional inert carrier, e.g. water, to produce the ultimate treating compositions. In general, good results can be obtained with liquid compositions containing from about 0.0001 to about 2.0 percent by weight of the toxicant in the final diluted form. With dusts, good results can usually be obtained with compositions containing from about 0.1 to about 2.0 percent or more by weight of toxicant. Where the compositions are to be applied to foliage of plants, it is preferred that the toxicant be present in an amount not to exceed about 0.8 percent in liquid compositions and about 1.0 percent in dusts. In terms of hectarage application, good controls of powdery mildews can be obtained when the active ingredients are applied to growing plants at a dosage of from about 0.004 to about 4 kg/hectare. When employed as fungicides for the treatment of seeds or non-living substrates, from about 0.1 to about 1 gram of morpholinyl silane per kilogram of substrate is an effective dose.

In the preparation of dust, or wettable powder compositions, the toxicant products can be compounded with any of the finely divided solids, such as prophyllite, talc, chalk, gypsum, fuller's earth, bentonite, attapulgite, starch, casein, gluten, or the like. In such operations, the finely divided carrier is ground or mixed with the toxicant or wet with a solution of the toxicant in a volatile organic solvent. Also, such compositions when employed as concentrates can be dispersed in water, with or without the aid of dispersing agents, to form spray mixtures. Dust compositions are advantageously employed when treating seeds.

Granular formulations are usually prepared by impregnating a solution of the toxicant in a volatile organic solvent onto a bed of coarsely divided attapulgite, bentonite, diatomite, or the like.

Similarly, the toxicant products can be compounded with a suitable water-immiscible inert organic liquid and a surface active dispersing agent to produce an emulsifiable concentrate which can be further diluted with water and oil to form spray mixtures in the form of oil-in-water emulsions which may optionally contain water miscible organic co-solvents to improve the physical properties of the formulation. In such compositions, the carrier comprises an aqueous emulsion, i.e., a mixture of inert water-immiscible solvent and optional water miscible organic co-solvent, emulsifying agent, and water.

Emulsifiers which can be advantageously employed herein can be readily determined by those skilled in the art and include various nonionic, anionic, cationic and amphoteric emulsifiers, or a blend of two or more emulsifiers. Examples of nonionic emulsifiers useful in preparing the emulsifiable concentrates include the polyalkylene glycol ethers and condensation products of alkyl and aryl phenols, aliphatic alcohols, aliphatic amines or fatty acids with ethylene oxide, propylene oxide or mixtures of ethylene and propylene oxides such as the ethoxylated alkyl phenols and carboxylic esters solubilized with the polyol or polyoxyalkylene. Cationic emulsifiers include quaternary ammonium compounds and fatty amines. Anionic emulsifiers include the oil-soluble salts (e.g., calcium) of alkylaryl sulphonic acids, oil soluble salts of sulphated polyglycol ethers and appropriate salts of phosphated polyglycol ether.

The preferred emulsifiers will depend upon the nature of the emulsifiable concentrate. For example, an emulsifiable concentrate of a compound of Formula I containing 200 g/l of the compound in xylene may require a blend of an ethoxylated nonyl phenol and calcium dodecyl benzene sulphonate to function effectively whereas a similar emulsifiable concentrate of the oleate salt of a compound of Formula I soluble in an aliphatic organic solvent will require a considerably different emulsification system.

Representative organic liquids which can be employed in preparing the emulsifiable concentrates of the present invention are the aromatic liquids such as xylene; propyl benzene fractions; or mixed naphthalene fractions; mineral oils substituted aromatic organic liquids such as dioctyl phthalate; kerosene; butene; dialkyl amides of various fatty acids, particularly the dimethyl amides of fatty glycols and glycol derivatives such as the n-butyl ether, ethyl ether or methyl ether of diethylene glycol, the methyl ether of triethylene glycol. Mixtures of two or more organic liquids are also often suitably employed in the preparation of the emulsifiable concentrate. The preferred organic liquids are xylene, and propyl benzene fractions, with xylene being most preferred. The surface active dispersing agents are usually employed in liquid compositions and in the amount of from 0.1 to 20 percent by weight of the combined weight of the dispersing agent and active compound. The active compositions can also contain other compatible additaments, for example, plant growth regulators and other biologically active compounds used in agriculture.

Especially, these active compositions may contain adjuvant surfactants to enhance the deposition, wetting and penetration of the composition onto the target crop and organism. These adjuvant surfactants may optionally be employed as a component of the formulation or as a tank mix. The amount of adjuvant surfactant will vary from 0.01 percent to 1.0 percent v/v based on a spray-volume of water, preferably 0.05 to 0.5 percent. Suitable adjuvant surfactants include ethoxylated nonyl phenols, ethoxylated synthetic or natural alcohols, salts of the esters of sulphosuccinic acids, ethoxylated organosilicones, ehtoxylated fatty amines and blends of surfactant with mineral or vegetable oils.

In such embodiments, the compounds of the present invention or compositions containing the same, can be advantageously employed in combination with one or more additional pesticidal compounds. Such additional pesticidal compounds may be insecticides, nematicides, miticides, arthropodicides, or bactericides that are compatible with the compounds of the present invention in the medium selected for application and not antagonistic to the activity of the present compounds. Accordingly, in such embodiments, the pesticidal compound is employed as a supplemental toxicant for the same or for a different pesticidal use or as an additament. The compounds in combination can generally be present in a ratio of from 1 to 100 parts of the compound of the present invention with from 100 to 1 part of the additional compound(s).

The exact amount of the active material to be applied is dependent not only on the specific active material being applied, but also on the particular action desired, the fungal species to be controlled and the stage of growth thereof as well as the part of the plant to be contacted with the toxic active ingredient. Thus, all of the active ingredients of the present invention and compositions containing the same may not be equally effective at similar concentrations or against the same fungal species.

The organosilanes employed in this invention can be prepared using known synthetic procedures. As an example, dimethylchlorosilane,

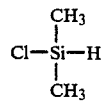

may be reacted with allyl chloride to form dimethyl-chloro-n-propylchlorosilane,

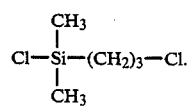

This product may then be reacted with an appropriate phenyl magnesium halide such as p-chlorophenyl magnesium bromide, to yield

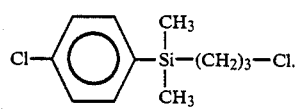

The reaction of this above product with 2,6-dimethylmorpholine yields dimethyl 3-(2,6-dimethyl-4-morpholino)-n-propyl-p-chlorophenylsilane of the formula

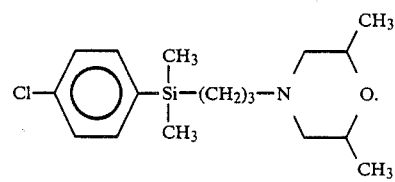

The following equations represent general method for preparing the organosilanes of the present invention.

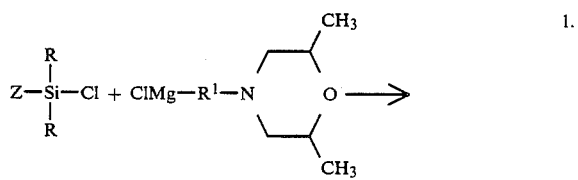

1.

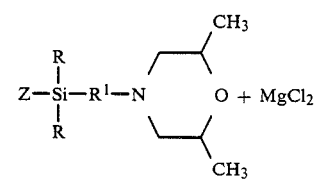

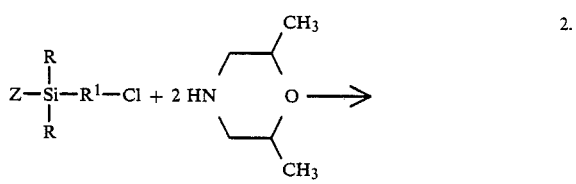

2.

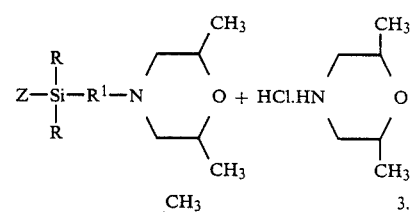

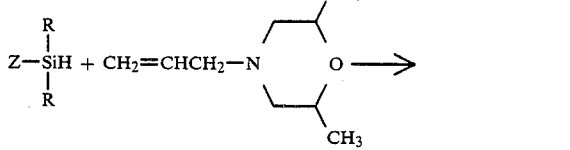

3.

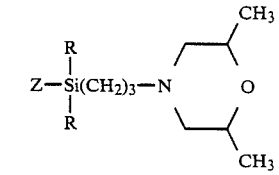

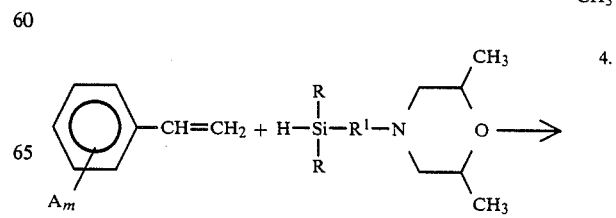

4.

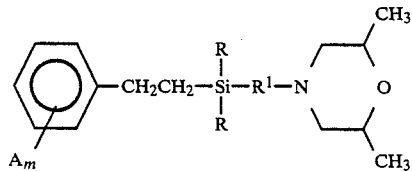

In the foregoing formula, Z is

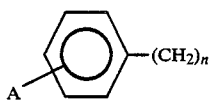

and A, n, R and R[1] are as previously defined.

The silanes employed as starting materials in the foregoing equations are either commercially available, particularly in those instances when A represents methyl, or can be synthesized using known preparative methods. Some of these methods are described in the following examples.

2,6-Dimethylmorpholine employed as a starting material and its cis- and trans- stereoisomers are well known and can be obtained commercially.

In the examples, all parts and percentages are by weight unless otherwise specified.

EXAMPLE 1

Dimethyl-3-(2,6-dimethyl-4-morpholino)-n-propyl-4-chlorophenethylsilane

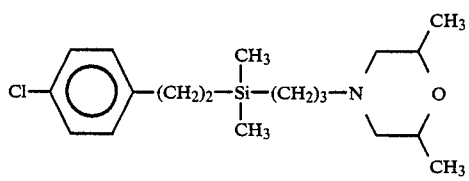

STEP A

Preparation of 3-(2,6-dimethyl-4-morpholino)-n-propyl magnesium chloride

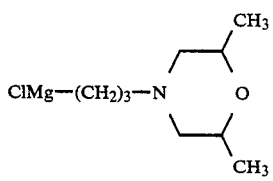

(a) A glass reactor equipped with a motor driven agitator, a thermometer and a water-cooled reflux condenser was charged with 315 g (2 mol) of 1-chloro-3-bromopropane. The contents of the reactor were heated to 50° C. and 461 g (4 mol) of 2,6-dimethyl-morpholine was gradually added. The temperature of the reaction mixture was maintained between 40° and 50° C. for 1½ hours, at which time heating was discontinued and the reaction mixture was allowed to cool to ambient temperature. A 500 ml portion of water and 500 ml of hexane were then added to the reaction mixture, followed by 90 g of sodium hydroxide. The organic phase of the resultant two-phase liquid was separated and retained. The aqueous phase was shaken together with 500 ml chloroform and the chloroform phase was separated and combined with the initial organic phase. The aqueous phase was discarded and the water present in the organic phase was removed using anhydrous magnesium sulfate. The solvents present in the liquid phase were evaporated under the reduced pressure supplied by a water aspirator. The residue was distilled under a pressure of 15 mm of mercury. The fraction boiling from 103° to 111° C. (vapor temperature) was collected and weighed 366.5 g. Analysis of this fraction by vapor phase chromatography indicated that it was 95 percent pure 4-(3-chloro-n-propyl)-2,6-dimethylmorpholine.

(b) A glass reactor was filled with nitrogen and charged with 2 g of magnesium chips, 25 ml of anhydrous tetrahydrofuran and a few drops of methyl iodide and ethylene dibromide. When a reaction initiated a small portion of a solution containing 192 g of the product obtained above in (a) and one liter of anhydrous tetrahydrofuran was added gradually until the reaction became self-sustaining. A 22 g portion of magnesium was then added to the reactor, following which the remainder of the aforementioned solution of 4-(3-chloro-n-propyl)-2,6-dimethylmorpholine in tetrahydrofuran was gradually added with slow agitation. External heating was employed as required to sustain the reaction. Following completion of the addition, the contents of the reactor were heated to the boiling point for 2 hours. The reaction mixture was allowed to cool under a nitrogen atmosphere. Magnesium was recovered in an amount of 1.7 g, indicating that the reaction was 92 percent completed.

STEP B

Preparation of dimethyl-3-(2,6-dimethyl-4-morpholino)-n-propylsilane

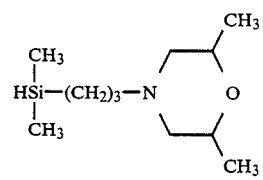

To a glass reactor, fitted with a motor driven agitator, thermometer, dropping funnel and water-cooled condenser, was added 29.2 g dimethylchlorosilane and 100 ml diethyl ether. While cooling the reactor with an ice-bath, 0.3 moles of the Grignard reagent prepared in (a) above was added dropwise via the dropping funnel over a period of 2 hours while keeping the reactor temperature between 10° and 20° C. The reaction mixture was allowed to stir overnight. To the reaction mixture was then added 300 ml of a 10 percent aqueous solution of citric acid with vigorous stirring. The mixture was transferred to a separatory funnel and the organic layer separated and evaporated to constant weight, leaving 68.0 g of a golden yellow liquid. On distillation of this liquid under vacuum, 60.9 g (93 percent) of a light yellow liquid boiling at 47°-50° at 0.2 mm was obtained. Infrared spectroscopy showed the presence of strong Si-H absorption and the NMR spectrum was consistent with the expected structure.

STEP C

Reaction of p-chlorostyrene with dimethyl-3-(2,6-dimethyl-4-morpholino)-n-propylsilane To a glass reactor fitted with a magnetic stirrer, thermometer and water-cooled reflux condenser was charged with 10.0 g of dimethyl-3-(2,6-dimethyl-4-morpholino)-n-propylsilane, 6.4 g of p-chlorostyrene and 0.1 g chloroplatinic acid in 1 ml isopropanol. The reaction mass was heated to 100° C. with stirring and kept at 100°-108° C. for ½ an hour, then cooled to room temperature. Low boiling impurities and unreacted starting materials were removed by distillation at 0.2 mm in an oil bath at 128° C. The residue was a light brown liquid and weighed 15.0 g. Analysis showed the compound to contain 8.0 percent silicon, 9.2 percent chlorine and 3.5 percent nitrogen. (The calculated values of silicon, chlorine and nitrogen for the compound are 7.9 percent, 10.0 percent and 3.9 percent, respectively.) The NMR spectrum was consistent with the expected structure (Compound I).

EXAMPLE 2

Dimethyl-3-(2,6-dimethyl-4-morpholino)-n-propyl-4-t-butylphenylsilane

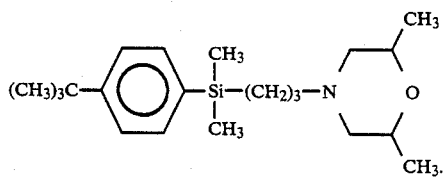

STEP A

Preparation of 3-chloro-n-propyldimethylchlorosilane

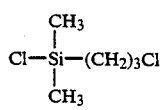

To a glass reactor equipped with a mechanically-driven stirrer, thermometer and dropping funnel was added 25 ml of a mixture of 1 ml of a 20 percent solution of chloroplatinic acid, 189.2 g dimethylchlorosilane and 157 g allyl chloride. The reaction mass was heated to 100° C. and the remainder of the chlorosilane/allyl chloride mixture was added dropwise over a period of 2 hours while maintaining the reaction mass at 80° C. After the addition was complete, the reaction mass was stirred for 1 hour at 80° C. and allowed to cool to room temperature.

The product was distilled at atmospheric pressure and the fraction boiling at 165°-175° C. was collected. It weighed 167.7 g and was a colorless, mobile liquid. Its NMR spectrum was consistent with the expected product.

STEP B

Preparation of 4-t-butylphenyl-3-chloro-n-propyldimethylsilane

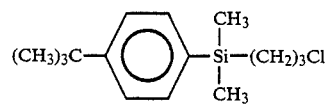

To a glass reactor fitted with a motor-driven stirrer, a thermometer, water-cooled reflux condenser and dropping funnel was charged 0.5 moles of 4-t-butylphenyl-magnesium bromide in THF (prepared in the usual manner from 4-t-butylbromobenzene, magnesium chips and tetrahydrofuran). While maintaining an atmosphere of nitrogen in the reactor, 64.0 g of 3-chloro-n-propyl-dimethylchlorosilane (prepared in Step A above) was added dropwise to the reactor over a period of 25 minutes, keeping the temperature between 35°-40° C. After the addition was complete, the mixture was stirred for 1 hour while allowing the reation temperature to drop to ~30°. To this mixture was added 400 ml of a 5 percent aqueous ammonium chloride solution. The organic layer was separated and dried over magnesium sulfate. After evaporation of solvent, the residue, weighing 113.6 g, was distilled under vacuum. The fraction boiling at 110°-120° C. at 0.5 mm was collected. It weighed 93.2 g and was a colorless, oily liquid of refractive index 1.5088 at 23° C. Analysis showed the compound to contain 67.4 percent carbon, 9.2 percent hydrogen and 13.0 percent chlorine. Theory for the compound is 67.0 percent carbon, 9.4 percent hydrogen and 13.2 percent chlorine. Gas chromatography showed the compound to be ~90 percent pure.

STEP C

Reaction of 4-t-butylphenyl-3-chloro-n-propyldimethylsilane with 2,6-dimethylmorpholine 15.0 G 4-t-butylphenyl-3-chloro-n-propyldimethylane (prepared in Step B above) and 13.0 g 2,6-dimethylmorpholine were charged to a glass reactor fitted with a reflux condenser, mechanical stirrer and thermometer. The mixture was refluxed for 3 hours, then cooled to room temperature. A solution containing 5 g sodium hydroxide in 50 ml water was added, followed by 25 ml diethyl ether with vigorous stirring. The organic phase was separated and dried over anhydrous magnesium sulfate. After evaporation of the solvent, the crude product was distilled under vacuum. The product fraction boiling at 163°-168° C. at 0.4 mm was collected. It was a yellow, oily liquid of refractive index 1.5017 and weighed 15.7 g. Analysis showed it to contain 72.8 percent carbon, 10.7 percent hydrogen and 3.8 percent nitrogen. Theory for the compound is 72.6 percent carbon, 10.7 percent hydrogen and 4.0 percent nitrogen. Gas chromatography showed the product to be 95 percent pure. Its NMR spectrum was consistent with the expected structure (Compound 2).

EXAMPLE 3

Dimethyl-3-(2,6-dimethyl-4-morpholino)-n-propyl-3,4-dichlorophenylsilane

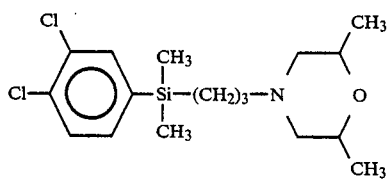

(a) Preparation of 3-(2,6-dimethyl-4-morpholino)-n-propyl magnesium chloride A glass reactor equipped with a motor driven agitator, a thermometer and a water-cooled reflux condenser was charged with 315 g (2 moles) of 1-chloro-3-bromopropane. The contents of the reactor were heated to 50° C. and 461 g (4 moles) of 2,6-dimethylmorpholine was gradually added. The temperature of the reaction mixture was maintained between 40° and 50° C. for 1½ hours, at which time heating was discontinued and the reaction mixture allowed to cool to ambient temperature. A 500 ml portion of water and 500 cc of hexane were then added to the reaction mixture, followed by 90 g of sodium hydroxide. The organic phase of the resultant two-phase liquid was separated and retained. The aqueous phase liquid was separated and retained. The aqueous phase was shaken together with 500 ml chloroform and the chloroform phase was separated and combined with the initial organic phase. The aqueous phase was discarded and the water present in the organic phase was removed using anhydrous magnesium sulfate. The solvents present in the liquid phase were evaporated under the reduced pressure supplied by a water aspirator. A solid precipitate formed in the residual liquid. The solid was removed by filtration and the filtrate was shaken together with an aqueous solution of sodium hydroxide. The aqueous layer was then separated, discarded and the water present in the organic layer was removed using anhydrous magnesium sulfate. The volatile materials were removed from the liquid phase by evaporation and the residue was distilled under a pressure of 15 to 41 mm of mercury. The fraction, boiling from 103° to 111° C. (vapor temperature), was collected and weighed 366.5 g. Analysis of this fraction by vapor phase chromatography indicated that it was 95 percent pure.

A glass reactor was filled with nitrogen and charged with 2 g of magnesium chips, 25 ml of anhydrous tetrahydrofuran and a few drops of methyl iodide and ethylene dibromide. When a reaction initiated, a small portion of a solution containing 192 g of the product obtained as described in the first paragraph of this example, and one liter of anhydrous tetrahydrofuran were added gradually until the reaction became self-sustaining. A 22 g portion of magnesium was then added to the reactor, following which the remainder of the aforementioned solution of N-(3-chloro-n-propyl)-2,6-dimethylmorpholine in tetrahydrofuran was gradually added with slow agitation. External heating was employed as required to sustain the reaction. Following completion of the addition, the contents of the reactor were heated to the boiling point for 2 hours without agitation. The reaction mixture was allowed to cool and then stored under a nitrogen atmosphere. A 1.7 g portion of magnesium was recovered, indicating that the reaction was 92 percent completed.

(b) Preparation of dimethyl(3,4-dichlorophenyl)-bromosilane

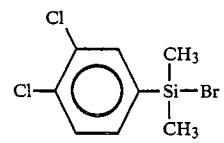

A glass reactor was filled with nitrogen and charged with 11 g (0.45 mole) of magnesium chips. A solution containing 100 g (0.44 mole) of 4-bromo-1,2-dichlorobenzene and 300 ml anhydrous diethyl ether was gradually added at a rate which maintained the reaction mixture at the boiling point. Following completion of the addition, external heating was applied to the reactor for 1 hour to maintain the reaction mixture at the boiling point. The mixture was then allowed to cool to ambient temperature and stored for about 16 hours, at which time 50 ml (0.45 mole) of dimethylchlorosilane were gradually added. An exothermic reaction accompanied the addition, following which the reaction mixture was stirred for 20 minutes at ambient temperature. The reaction product was then hydrolyzed using an aqueous solution of ammonium chloride and the aqueous phase of the resultant two-phase liquid was separated and discarded. The water present in the organic layer was removed using anhydrous magnesium sulfate, following which the organic solvents were removed from the liquid phase by evaporation under reduced pressure. The residue was then distilled under a pressure of from 0.1 to 0.2 mm of mercury and the fraction, boiling from 48° to 60° C. (vapor temperature), was collected. This fraction weighed 83.2 g (equivalent to a yield of 92 percent) and was found to contain 47.56 percent carbon, 5.02 percent hydrogen and 33.60 percent chlorine. The calculated values for the expected product, dimethyl(3,4-dichlorophenyl)silane, are 46.8 percent, 4.9 percent and 34.6 percent, respectively.

A glass reactor was charged with 19.1 g (0.093 mole) of dimethyl(3,4-dichlorophenyl)silane and 200 ml of petroleum ether. This mixture was cooled to −10° C., at which time a solution containing 14.9 g (0.093 mole) of bromine and 200 ml petroleum ether was gradually added, with agitation, to the reaction mixture. A decolorization of the bromine was observed. The cooling bath was removed as the bromine addition progressed. The resultant reaction mixture was stirred for 1 hour at ambient temperature following completion of the bromine addition. The volatile materials present in the reaction mixture were removed by evaporation under reduced pressure. The residue weighed 26.3 g, which is equivalent to a yield of 100 percent.

(c) Reaction of dimethyl-3,4-dichlorophenylbromosilane with 3-(2,6-dimethylmorpholino)-n-propylmagnesium chloride A glass reactor was charged with the Grignard reagent prepared as described in part (a) of this example under a nitrogen atmosphere. A 50 ml portion of anhydrous tetrahydrofuran was added to the reactor, followed by the gradual addition of the bromosilane prepared as described in part (b) of this example. Upon completion of this addition, the contents of the reactor were stirred and maintained under ambient conditions for about 64 hours, at which time an aqueous solution of ammonium chloride was added to the contents of the reactor. The organic phase was then separated, the water present therein was removed using anhydrous magnesium sulfate and the volatile solvents were evaporated under reduced pressure. The residue, which weighed 40.8 g, was then distilled under a pressure of 0.15 mm of mercury and the fraction, boiling from 150° to 157° C. (vapor temperature), was collected and analyzed. This fraction was found to contain 56.49 percent carbon, 7.59 percent hydrogen and 19.52 percent chlorine. The calculated values for the expected product, represented by the formula

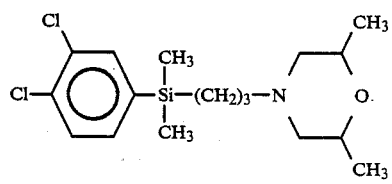

are 56.7 percent, 7.5 percent and 19.7 percent, respectively (Compound 3).

EXAMPLE 4

Dimethyl-4-(2,6-dimethyl-4-morpholino)-n-butyl-4-chlorobenzylsilane

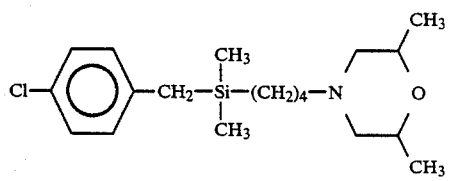

STEP A

Preparation of 4-chlorobenzyldimethyl-4-chloro-n-butylsilane

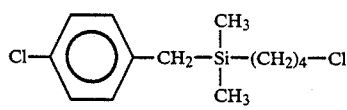

In a 500 ml glass reactor fitted with a mechanically driven stirrer, thermometer, nitrogen inlet, dropping funnel and water-cooled reflux condenser was charged 7.9 g magnesium chip. Via the dropping funnel was added a solution of 47.5 g 4-chlorobenzyl chloride in 200 ml diethyl ether with stirring over a period of ½ an hour. After the addition was complete, the reaction was refluxed for ½ hour, then cooled to room temperature. To the Grignard reagent was added a solution of 31.0 g chlorodimethyl-4-chloro-n-butylsilane (Petrarch Systems Inc., Bristol, PA) in 50 ml ether. The reaction mixture was refluxed for 1 hour after the addition was complete, then cooled to room temperature. A solution of 10 g citric acid in 200 ml water was added to hydrolyze the reaction. The organic layer was separated, dried over magnesium sulfate and the solvent removed at room temperature under vacuum. Low boiling impurities were removed by distillation at 150° C. under 15 mm vacuum. The residue was a yellow oil. Vapor phase chromatography showed the compound to be about 95 percent pure. Its NMR spectrum was consistent with the expected compound.

STEP B

Reaction of 4-chlorobenzyldimethyl-4-chloro-n-butylsilane with 2,6-dimethyl morpholine In a 250 ml glass reactor equipped with a magnetic stirrer, water-cooled reflux condenser and thermometer was charged 30.0 g 4-chloro-n-butyldimethyl-4-chlorobenzylsilane and 8.3 g 2,6-dimethylmorpholine. The mixture was heated with stirring to 80° and held at this temperature for 1 hour. The temperature was raised to 100° C. for 4 hours, then to 120° for 2 hours, followed by an additional 3 hours heating at 160° C. On cooling to room temperature, the product partially solidified. To the mixture 500 ml diethyl ether was added with vigorous stirring. The mixture was filtered and the solid residue was resuspended in 300 ml of ethyl ether and cooled to 15° C. To the stirred ether suspension, 250 ml of a 3 percent aqueous solution of sodium hydroxide was added over 15 minutes. The organic phase was separated, dried over magnesium sulfate and the solvent evaporated off, leaving 10.3 g of a brownish oil. The product contained 8.7 percent chlorine by combustion analysis. Theory for the compound is 10.0 percent. Gas phase chromatography showed the compound to be about 92 percent pure. The NMR spectrum was consistent with the expected product (Compound 4).

EXAMPLE 5

Dimethyl-3-(2,6-dimethyl-4-morpholino)-n-propyl-3-(trifluoromethyl)phenylsilane.

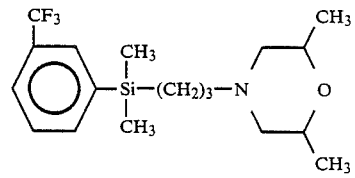

STEP A

Preparation of 3-(trifluoromethyl)phenyl-3-chloro-n-propyldimethylsilane.

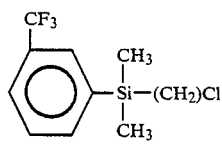

To a solution of 3-(trifluoromethyl)phenylmagnesium bromide (prepared from 40.5 g 3-bromobenzotrifluoride, 3.8 g magnesium chips and 100 ml tetrahydrofuran) contained in a glass reactor fitted with a mechanical stirrer, water-cooled reflux condenser, thermometer and dropping funnel, was added dropwise with stirring 25.0 g 3-chloro-n-propyldimethylchlorosilane (prepared as in 2 (a) above)) while maintaining the temperature of the reaction at 35°. On completion of the addition, the reaction mixture was refluxed for 1 hour, then cooled to room temperature. To the reaction mixture was added 300 ml of a 10 percent aqueous solution of citric acid with vigorous stirring. The organic layer was separated, dried and evaporated to leave 55.6 g of yellow oil. Distillation of this crude product under vacuum yielded 35.0 g of a colorless liquid boiling at 77°–91° C. at 0.4 mm of index of refraction 1.4714 at 23° C. The product contained 50.9 percent carbon, 5.6 percent hydrogen and 12.4 percent chlorine. Theory for the expected compound is 51.3 percent carbon, 5.7 percent hydrogen and 12.6 percent chlorine. The product was about 93 percent pure by gas chromatography.

STEP B

Reaction of 3-(trifluoromethyl)phenyl-3-chloro-n-propylidimethylsilane with 2,6-dimethyl morpholine.

To a glass reactor fitted with a magnetic stirrer, water-cooled reflux condenser and thermometer was added 15.5 g of 3-(trifluoromethyl)phenyl-3-chloro-n-propyldimethylsilane and 15.0 g 2,6-dimethylmorpholine. The mixture was refluxed for 1 hour, then cooled to room temperature. To the brown mixture was added a solution of 5 g sodium hydroxide in 50 ml water, followed by 50 ml hexane. The organic phase was separated, dried and the solvent removed at room temperature under vacuum. The residue, a brown oil, was distilled under vacuum and the fraction boiling at 112°–129° C. at 0.35 mm was collected. It was a light yellow liquid of refractive index 1.4735 at 23° C. Gas chromatography showed the compound to be greater than 95 percent pure. It contained 60.9 percent carbon, 8.1 percent hydrogen and 3.8 percent chlorine by analysis. Theory for the compound is 60.1 percent carbon, 7.8 percent hydrogen and 3.9 percent chlorine. The NMR spectrum was consistent with the expected structure (Compound 5).

EXAMPLE 6

Dimethyl 3-(2,6-dimethyl-4-morpholino)-n-propyl-4-chlorophenylsilane

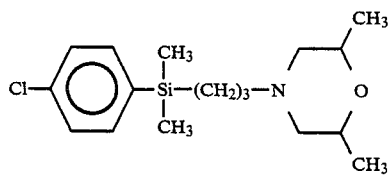

A glass reactor was filled with nitrogen and charged with 281 g (0.485 mole) of p-chlorophenylmagnesium chloride prepared by reacting p-chlorobromobenzene with magnesium chips using anhydrous diethyl ether as the reaction medium. An 83 g portion of dimethylchloro-3-chloro-n-propylsilane, prepared as described in the preceding Example 2, was gradually added to the reaction. Following completion of the addition, the contents of the reactor were heated to the boiling point until most of the diethyl ether was removed by distillation. A 150 ml portion of anhydrous tetrahydrofuran was added to the reactor and the resultant mixture was heated at the boiling point for 1 hour. The reaction mixture was then combined with a stoichiometric excess of an aqueous ammonium chloride solution, the organic phase was removed and the aqueous phase was extracted with 200 ml of hexane. The hexane layer was combined with the original organic layer and the water present was removed using anhydrous magnesium sulfate. The solvents and other volatile materials were removed under reduced pressure and the residue was distilled under a pressure of 0.1 mm of mercury. The fraction, boiling from 90° to 102° C., was collected. This fraction, which weighed 95.1 g, was found to contain 52.84 percent carbon, 6.62 percent hydrogen and 28.15 percent chlorine. The calculated values for the expected product, 3-chloro-n-propyl-4-chlorophenyldimethylsilane, are 53.42 percent, 6.51 percent and 28.71 percent, respectively. A 10 g portion of this material and 25 g of 2,6-dimethylmorpholine were charged into a glass reactor and heated to a temperature of from 120° to 130° C. for 3½ hours. After the contents of the flask had cooled to ambient temperature, a small amount of diethyl ether was added to dissolve the material in the reactor. The resultant solution was evaporated under reduced pressure to remove the diethyl ether and the residue was distilled under a pressure of 0.3 mm of mercury. The fraction, boiling from 127° to 150° C. (vapor temperature), was collected. This portion, which weighed 9.7 g, was found to contain 62.7 percent carbon, 8.58 percent hydrogen and 10.33 percent chlorine. The calculated values for the expected product, dimethyl-3-(2,6-dimethyl-4-morpholino)-n-propyl-4-chlorophenylsilane, are 62.6 percent, 8.7 percent and 10.9 percent, respectively (Compound 6).

Employing the above procedures and the appropriate starting materials, the following compounds were prepared:

| Compound No. | |
| --- | --- |
| 7 | dimethyl-3-(2,6-dimethyl-4-morpholino)-η-propyl-2,6-dichlorobenzylsilane |
| 8 | dimethyl-3-(2,6-dimethyl-4-morpholino)-η-propyl-2-chlorobenzylsilane |
| 9 | dimethyl-3-(2,6-dimethyl-4-morpholino)-η-propylphenylsilane |
| 10 | dimethyl-3-(2,6-dimethyl-4-morpholino)-η-propyl-4-chlorobenzylsilane |
| 11 | dimethyl-3-(2,6-dimethyl-4-morpholino)-η-propyl-4-phenoxyphenylsilane |
| 12 | dimethyl-3-(2,6-dimethyl-4-morpholino-η-propyl-4-methoxyphenylsilane |

The organosilanes disclosed in the preceding examples were evaluated for fungicidal activity by applying the test compound, in diluted form, to a host plant. The plants were inoculated with the fungus (in spore form) and stored in a greenhouse or other controlled environment until untreated plants, used as controls, became infested with the fungus. The treated plants were then visually inspected and assigned a rating based on the percentage of total leaf area that had not become infested.

Formulations containing the test compounds were prepared from concentrates in acetone. The silane compound (0.04 g) was dissolved in 10 ml of acetone and 90 ml of water and 2 drops of a wetting agent were added to form a 400 ppm solution of the morpholinyl silane for application to leaves or roots.

The specific procedures employed in vivo to evaluate the test compounds against particular fungi are described in the following paragraphs.

---
Procedure A - Barley Powdery Mildew
- Foliar and Soil Drench Test
---

Approximately 10 barley seeds (cv. Golden Promise) were sown at a depth of ½ inch into a 3-inch plastic pot containing sterilized loam soil. The pots were maintained under greenhouse conditions until the barley had germinated and reached a height of 3 to 5 inches. The foliage was then sprayed with a 400 ppm solution of the test chemical and 10 ml of the same chemical applied as a soil drench at a concentration of 400 ppm to each pot. The treated plants were held under greenhouse conditions for 24 hours and then inoculated with conidia of *Erysiphe graminis hordeii* by brushing the foliage with heavily sporulating plants.

The plants were assessed for disease levels after 5 to 8 days when the treated, inoculated tests showed good disease levels.

---
Procedure B - Barley Powdery Mildew
- Eradicant Test, Foliar Application
---

Barley was grown as for the foliar and soil drench test. Plants were inoculated by dry dusting of spores from heavily infested plants and then maintained under greenhouse conditions for 3 days. They were then sprayed with a 100 ppm solution of the test chemical onto the leaves. The plants were maintained under greenhouse conditions and the symptoms assessed 5 to 8 days later by comparing the sporulation on plants treated with experimental chemical to untreated but uninoculated plants.

onto the leaves. The plants were placed into a chamber with 100 percent relative humidity for 48 hours and then removed and held in a greenhouse for 5 to 7 days and assessed when symptoms of the disease appeared on the untreated, inoculated plants.

The results of test of procedures A, B and C are set forth hereinafter in Table I.

TABLE 1

| | IN VIVO BIOLOGICAL EVALUATION PERCENT EFFICACY OF THE COMPOUNDS IN VIVO | | |
|---|---|---|---|
| COM-POUND NUM-BER | BARLEY POWDERY MILDEW (PROCE-DURE A) | BARLEY POWDERY MILDEW (PROCE-DURE B) | RICE BLAST (PROCE-DURE C) |
| 1 | 100 | 90 | 100 |
| 2 | 100 | NT | NT |
| 4 | 97 | NT | NT |
| 5 | 100 | NT | NT |
| 8 | 100 | 90 | 100 |
| 9 | 93 | NT | NT |
| 10 | 100 | 75 | 100 |
| 11 | 100 | NT | NT |

NT - not Tested

Procedure D - in vitro test against 8 organisms

Test chemicals were added to liquid potato dextrose agar in plastic petri dishes at a final concentration of 40 ppm and then the agar allowed to cool and set to a solid. Discs of actively growing fungi of the following plants pathogenic species: *Alternaria brassisicola* (leaf spot), *Pyricularia oryzae*, *Fusarium oxysporum f. sp. phaseolicola*, *Pyrenophora teres* (net blotch), *Phytophthora citricola*, *Rhizoctonia cerealis*, *Colletotrichum coffeanum* and *Verticillium albo-atrum* were placed onto the chemical incorporated agar. Radial growth of the fungi was measured after 3-5 days when growth of the fungi on the untreated agar had reached a maximum. The results of said test are set forth hereinafter in Table 2.

TABLE 2

| | IN VITRO BIOLOGICAL EVALUATION PERCENT EFFICACY OF THE COMPOUNDS (PROCEDURE D) | | | | | | | |
|---|---|---|---|---|---|---|---|---|
| COM-POUND EXAM-PLE | ALTER-NARIA BRASS-ISICOLA | PYRICU-LARIA ORYZAE | FUSA-RIUM OXY SPORUM | PYRENO-PHORA TERES | PHYTO-PHTHORA PARA-SITICA | RHIZOC-TONIA CEREALIS | COLLETO-TRICHUM COFFEANUM | VERTI-CILLIUM ALBO-ATRUM |
| 1 | 100 | 100 | 70 | 100 | 59 | 100 | 79 | 100 |
| 2 | 88 | 100 | 68 | 93 | 87 | 96 | 45 | 90 |
| 4 | 96 | 100 | 73 | 100 | 93 | 96 | 82 | 90 |
| 5 | 96 | 100 | 27 | 100 | 20 | 86 | 39 | 100 |
| 8 | 100 | 100 | 26 | 80 | 0 | 100 | 33 | 100 |
| 9 | 80 | 100 | 0 | 77 | 7 | 39 | 9 | 81 |
| 10 | 100 | 100 | 40 | 100 | 12 | 100 | 49 | 100 |
| 11 | 63 | 100 | 68 | 81 | 80 | 71 | 70 | 33 |

---
Procedure C - Rice Blast
- Foliar and Soil Drench Test
---

Approximately 10 seeds of barley (cv. Golden Promise) were sown at a depth of ½ inch into a 3-inch plastic pot containing sterilized loam. The pots were maintained under greenhouse conditions until the plants had germinated and reached a height of 3-5 inches. The foliage was then sprayed with a test chemical at a 400 ppm concentration in solution and 10 ml of this same solution was poured onto the soil of each pot. The treated plants were held in a greenhouse for 24 hours and then inoculated with $1 \times 10^6$ conidia per ml of *Pyricularia oryzae* (rice blast) by spraying the spores In other in vivo tests, compound numbers 1, 4, 5, 9, 10, 11 and 12 were found to give at 400 ppm at least 80 percent kill and control of *Erysiphe graminis* when plants were sprayed with the test compound prior to inoculation with spores of the fungal organism. In other tests, compound numbers 1, 4, 9 and 11 at 400 ppm gave at least 80 percent kill and control of *Puccinia recondita* when the plants were inoculated with spores of the fungal organism prior to being sprayed with the test compound.

When some of the compounds were applied at dosage levels of between 2 and 400 ppm, they had the ability to kill, inhibit or otherwise control one or more fungal diseases of plants.

What is claimed is:

1. A compound corresponding to the formula

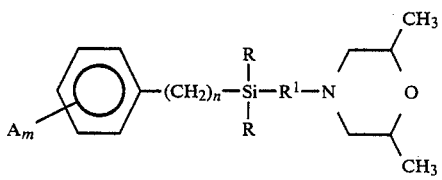

wherein:
  each A independently represents halogen, $C_1$–$C_4$ alkyl, $C_1$–$C_4$ alkoxy, phenyl, phenoxy or halomethyl;
  each R independently represents $C_1$–$C_4$ alkyl;
  n represents the integer 0, 1 or 2;
  m represents the integer 0 to 5; and
  $R^1$ represents an alkylene group of the formula

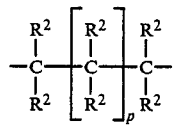

where each $R^2$ independently represents hydrogen or $C_1$–$C_3$ straight chain alkyl and p represents an integer of from 1 to 4, with the proviso that the total number of carbon atoms in $R^1$ is from 3–6.

2. A compound as defined in claim 1 wherein p is 1.

3. A compound as defined in claim 2 wherein n is 0.

4. The compound as defined in claim 3 which is dimethyl-(3-(2,6-dimethyl-4-morpholino)-n-propyl)-phenylsilane.

5. The compound as defined in claim 3 which is dimethyl-3-(2,6-dimethyl-4-morpholino)-n-propyl-4-chlorophenylsilane.

6. The compound as defined in claim 3 which is dimethyl-3-(2,6-dimethyl-4-morpholino)-n-propyl-3,4-dichlorophenylsilane.

7. The compound as defined in claim 3 which is dimethyl-3-(2,6-dimethyl-4-morpholino)-n-propyl-4-methoxyphenylsilane.

8. The compound as defined in claim 3 which is dimethyl-3-(2,6-dimethyl-4-morpholino)-n-propyl-4-phenoxyphenylsilane.

9. The compound as defined in claim 3 which is dimethyl-3-(2,6-dimethyl-4-morpholino)-n-propyl-4-t-butylphenylsilane.

10. The compound as defined in claim 3 which is dimethyl-3-(2,6-dimethyl-4-morpholino)-n-propyl-3-(trifluoromethyl)phenylsilane.

11. A compound as defined in claim 2 wherein n is 1.

12. The compound as defined in claim 11 which is dimethyl-3-(2,6-dimethyl-4-morpholino)-n-propyl-2-chlorobenzylsilane.

13. The compound as defined in claim 11 which is dimethyl-3-(2,6-dimethyl-4-morpholino)-n-propyl-4-chlorobenzylsilane.

14. The compound as defined in claim 11 which is dimethyl-3-(2,6-dimethyl-4-morpholino)-n-propyl-2,6-dichlorobenzylsilane.

15. The compound as defined in claim 11 which is dimethyl-4-(2,6-dimethyl-4-morpholino)-n-butyl-4-chlorobenzylsilane.

16. A compound as defined in claim 2 wherein n is 2.

17. The compound as defined in claim 16 which is dimethyl-3-(2,6-dimethyl-4-morpholino)-n-propyl-4-chlorophenethylsilane.

18. A fungicidal composition which comprises an inert adjuvant in intimate admixture with at least a fungicidally effective amount of a morpholinyl compound, as the active material, which corresponds to the formula

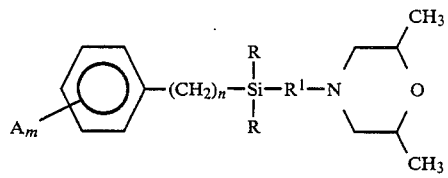

wherein:
  each A independently represents halogen, $C_1$–$C_4$ alkyl, $C_1$–$C_4$ alkoxy, aryloxy or halomethyl;
  each R independently represents $C_1$–$C_4$ alkyl;
  n represents the integer 0, 1 or 2;
  m represents the integer 0 to 5; and
  $R^1$ represents an alkylene group of the formula

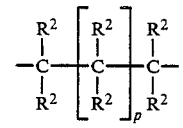

where each $R^2$ independently represents hydrogen or $C_1$–$C_3$ straight chain alkyl and p represents an integer of from 1 to 4, with the proviso that the total number of carbon atoms in $R^1$ is from 3–6.

19. A composition as defined in claim 18 wherein p is 1.

20. A composition as defined in claim 19 wherein n is 0.

21. The composition as defined in claim 20 wherein the active material is dimethyl-(3-(2,6-dimethyl-4-morpholino)-n-propyl)phenylsilane.

22. The composition as defined in claim 20 wherein the active material is dimethyl-3-(2,6-dimethyl-4-morpholino)-n-propyl-4-chlorophenylsilane.

23. The composition as defined in claim 20 wherein the active material is dimethyl-3-(2,6-dimethyl-4-morpholino)-n-propyl-3,4-dichlorophenylsilane.

24. The composition as defined in claim 20 wherein the active material is dimethyl-3-(2,6-dimethyl-4-morpholino)-n-propyl-4-methoxyphenylsilane.

25. The composition as defined in claim 20 wherein the active material is dimethyl-3-(2,6-dimethyl-4-morpholino)-n-propyl-4-phenoxyphenylsilane.

26. The composition as defined in claim 20 wherein the active material is dimethyl-3-(2,6-dimethyl-4-morpholino)-n-propyl-4-t-butylphenylsilane.

27. The composition as defined in claim 20 wherein the active dimethyl-3-(2,6-dimethyl-4-morpholino)-n-propyl-3-(trifluoromethyl)phenylsilane.

28. A composition as defined in claim 19 wherein n is 1.

29. The composition as defined in claim 28 wherein the active material is dimethyl-3-(2,6-dimethyl-4-morpholino)-n-propyl-2-chlorobenzylsilane.

30. The composition as defined in claim 28 wherein the active material is dimethyl-3-(2,6-dimethyl-4-morpholino)-n-propyl-4-chlorobenzylsilane.

31. The composition as defined in claim 28 wherein the active material is dimethyl-3-(2,6-dimethyl-4-morpholino)-n-propyl-2,6-dichlorobenzylsilane.

32. The composition as defined in claim 28 wherein the active material is dimethyl-4-(2,6-dimethyl-4-morpholino)-n-butyl-4-chlorobenzylsilane.

33. A composition as defined in claim 19 wherein n is 2.

34. The composition as defined in claim 33 wherein the active material is dimethyl-3-(2,6-dimethyl-4-morpholino)-n-propyl-4-chlorophenethylsilane.

35. A composition as defined in claim 18 which is in the form of an emulsifiable concentrate, a flowable concentrate, a wettable powder or a granular formulation.

36. A composition as defined in claim 35 which contains from about 2 to about 95 percent by weight of the morpholinyl silane compound.

37. A composition as defined in claim 35 which contains from about 10 to about 60 percent by weight of the morpholinyl silane compound.

38. A composition as defined in claim 35 which is in the form of a wettable powder.

39. A composition as defined in claim 38 which contains from about 2 to about 10,000 ppm of the morpholinyl silane compound.

40. A composition as defined in claim 39 which contains from about 10 to about 600 ppm of the morpholinyl silane compound.

41. A method for the kill and control of fungi which attack plants or plant parts which comprises applying to plants or plant parts a fungicidally effective amount of a composition which comprises an inert adjuvant in intimate admixture with a morpholinyl compound, as the active material, which corresponds to the formula

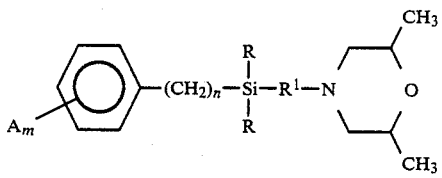

wherein:
each A independently represents halogen, $C_1$–$C_4$ alkyl, $C_1$–$C_4$ alkoxy, aryloxy or halomethyl;
each R independently represents $C_1$–$C_4$ alkyl;
n represents the integer 0, 1 or 2;
m represents the integer 0 to 5; and
$R^1$ represents an alkylene group of the formula

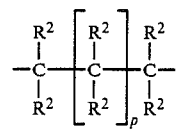

where each $R^2$ independently represents hydrogen or $C_1$–$C_3$ straight chain alkyl and p represents an integer of from 1 to 4, with the proviso that the total number of carbon atoms in $R^1$ is from 3–6.

42. A method as defined in claim 41 wherein p is 1.

43. A method as defined in claim 42 wherein n is 0.

44. The method as defined in claim 43 wherein the active material is dimethyl-(3-(2,6-dimethyl-4-morpholino)-n-propyl)phenylsilane.

45. The method as defined in claim 43 wherein the active material is dimethyl-3-(2,6-dimethyl-4-morpholino)-n-propyl-4-chlorophenylsilane.

46. The method as defined in claim 43 wherein the active material is dimethyl-3-(2,6-dimethyl-4-morpholino)-n-propyl-3,4-dichlorophenylsilane.

47. The method as defined in claim 43 wherein the active material is dimethyl-3-(2,6-dimethyl-4-morpholino)-n-propyl-4-methoxyphenylsilane.

48. The method as defined in claim 43 wherein the active material is dimethyl-3-(2,6-dimethyl-4-morpholino)-n-propyl-4-phenoxyphenylsilane.

49. The method as defined in claim 43 wherein the active material is dimethyl-3-(2,6-dimethyl-4-morpholino)-n-propyl-4-t-butylphenylsilane.

50. The method as defined in claim 43 wherein the active material is dimethyl-3-(2,6-dimethyl-4-morpholino)-n-propyl-3-(trifluoromethyl)phenylsilane.

51. A method as defined in claim 42 wherein n is 1.

52. The method as defined in claim 51 wherein the active material is dimethyl-3-(2,6-dimethyl-4-morpholino)-n-propyl-2-chlorobenzylsilane.

53. The method as defined in claim 51 wherein the active material is dimethyl-3-(2,6-dimethyl-4-morpholino)-n-propyl-4-chlorobenzylsilane.

54. The method as defined in claim 51 wherein the active material is dimethyl-3-(2,6-dimethyl-4-morpholino)-n-propyl-2,6-dichlorobenzylsilane.

55. The method as defined in claim 51 wherein the active material is dimethyl-4-(2,6-dimethyl-4-morpholino)-n-butyl-4-chlorobenzylsilane.

56. A method as defined in claim 42 wherein n is 2.

57. The method as defined in claim 56 wherein the active material is dimethyl-3-(2,6-dimethyl-4-morpholino)-n-propyl-4-chlorophenethylsilane.

* * * * *